US00PP35804P2

(12) United States Plant Patent
van Zoest

(10) Patent No.: US PP35,804 P2
(45) Date of Patent: May 14, 2024

(54) ***CLEMATIS* PLANT NAMED 'ZO18197'**

(50) Latin Name: ***Clematis* hybrid**
Varietal Denomination: Zo18197

(71) Applicant: Jos van Zoest, Boskoop (NL)

(72) Inventor: Jos van Zoest, Boskoop (NL)

(73) Assignee: J.VAN ZOEST BEHEER B.V., Boskoop (NL)

( * ) Notice: Subject to any disclaimer, the term of this patent is extended or adjusted under 35 U.S.C. 154(b) by 0 days.

(21) Appl. No.: 18/225,127

(22) Filed: Jul. 22, 2023

(30) Foreign Application Priority Data

May 1, 2023 (QZ) ..... PBR 20230945

(51) Int. Cl.
*A01H 5/02* (2018.01)
*A01H 6/72* (2018.01)

(52) U.S. Cl.
USPC ..... Plt./228

(58) Field of Classification Search
USPC ..... Plt./228
See application file for complete search history.

*Primary Examiner* — Susan McCormick Ewoldt
*Assistant Examiner* — Zachariah Allan Kay
(74) *Attorney, Agent, or Firm* — Penny J. Aguirre

(57) ABSTRACT

A new cultivar of hybrid *Clematis* plant named 'Zo18197' that is characterized by its floriferous and long blooming habit; June to September in The Netherlands, its flowers on young plants that appear from the base to the top of the plant, its dark grey-green anthers, and its flowers that are deep violet-blue in color with an axillary central band on each tepal that is slightly lighter in color.

3 Drawing Sheets

Botanical classification: *Clematis* hybrid.
Variety denomination: 'Zo18197'.

BACKGROUND OF THE INVENTION

The present invention relates to a new and distinct cultivar of *Clematis* plant of hybrid origin and will be referred to hereafter by its cultivar name 'Zo18197'. 'Zo18197' is an herbaceous perennial grown for use as a landscape plant.

'Zo18197' originated as a seedling that arose from seed planted from open pollination of an unnamed and unpatented plant of *Clematis* from the Inventor's breeding program, reference no. 19960173, in August of 2018. The male parent is unknown. The new *Clematis* was selected as a single unique plant in June of 2019 from the resulting seedlings.

Asexual propagation of the new cultivar was first accomplished by softwood stem cuttings under the direction of the Inventor in June of 2019 in Boskoop, The Netherlands. Asexual propagation by softwood stem cutting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish *Clematis* 'Zo18197' as a unique cultivar of *Clematis*.

1. 'Zo18197' exhibits floriferous and long blooming habit; June to September in The Netherlands.
2. 'Zo18197' exhibits flowers on young plants that appear from the base to the top of the plant.
3. 'Zo18197' exhibits dark grey-green anthers.

4. 'Zo18197' exhibits flowers that are deep violet-blue in color with an axillary central band on each tepal that is slightly lighter in color.

The female parent of 'Zo18197' differs from 'Zo18197' in having flowers that are smaller in size, lighter in color, does not have the central axillary stripe on each tepal, and a much shorter flowering period. 'Zo18197' can be most closely compared to the *Clematis* cultivars 'Daniel Deronda' (not patented), 'The President' (not patented), and 'Zo18179'. 'Daniel Deronda' and 'The President' are both similar to 'Zo18197' in flower color. 'Daniel Deronda' differs from 'Zo18197' in producing less flowers and having a shorter blooming period, anthers that are creamy white in color, and flowers on young plants that are present only on the top half of the plant. 'The President' differs from 'Zo18197' in producing less flowers and having a shorter blooming period, a shorter plant height, and flowers on young plants that are present only on the top half of the plant. 'Zo18179' is similar to 'Zo18197' in having a central axillary stripe on each tepal and flowers that appear from the base to the top of the plant. 'Zo18179' differs from 'Zo18197' in having flowers that are violet in color with a purple central axillary stripe on each tepal and dark purple anthers.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosures and/or sales that fall within a one-year grace period to the filing date. Disclosures include website listings by Plantarium/ groen-Direkt, Esveld Shop, AIPH, Debloeimeesters, Facebook (Plantkeuze), Promesse de fleurs, J. van Zoest BV, Zahradaweb, Jardin du Pic Vert, Camolin Potting Shed, FlorAccess, Horticulture Week, Plantago, and Bloemenkrant.

BRIEF DESCRIPTION OF THE DRAWINGS

The accompanying color photographs illustrate the overall appearance and distinct characteristics of the new *Clematis*. The photographs were taken of a 15-month-old plant as grown outdoors in a 13-cm container in Boskoop, The Netherlands The photograph in FIG. 1 provides a side view of 'Zo18197' in bloom.

The photograph in FIG. 2 provides a close-up view of a flower of 'Zo18197'.

Figure 1:
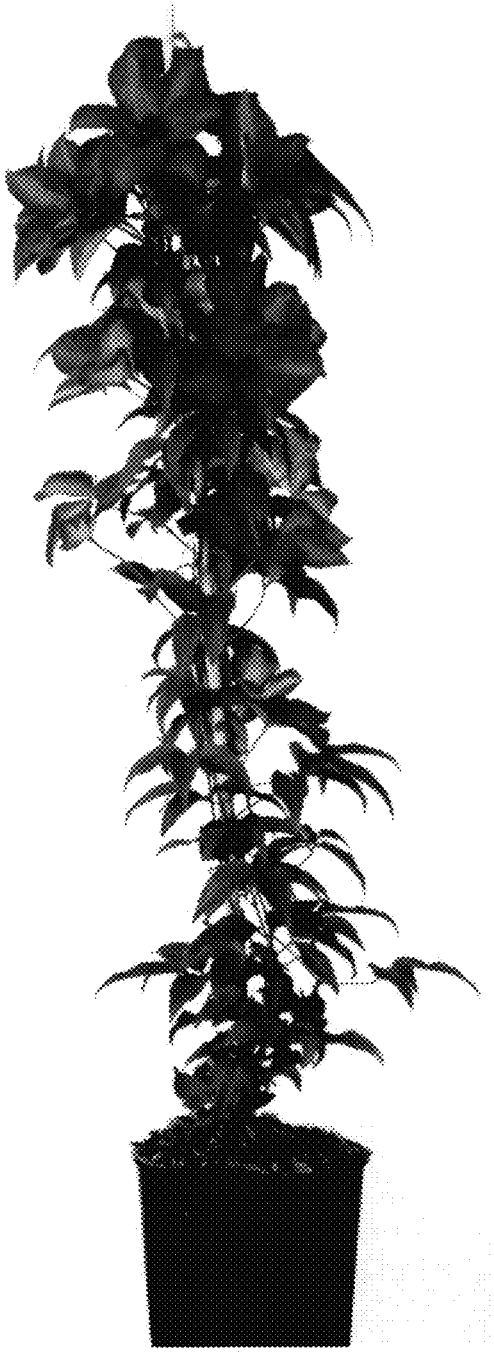
Figure 2:
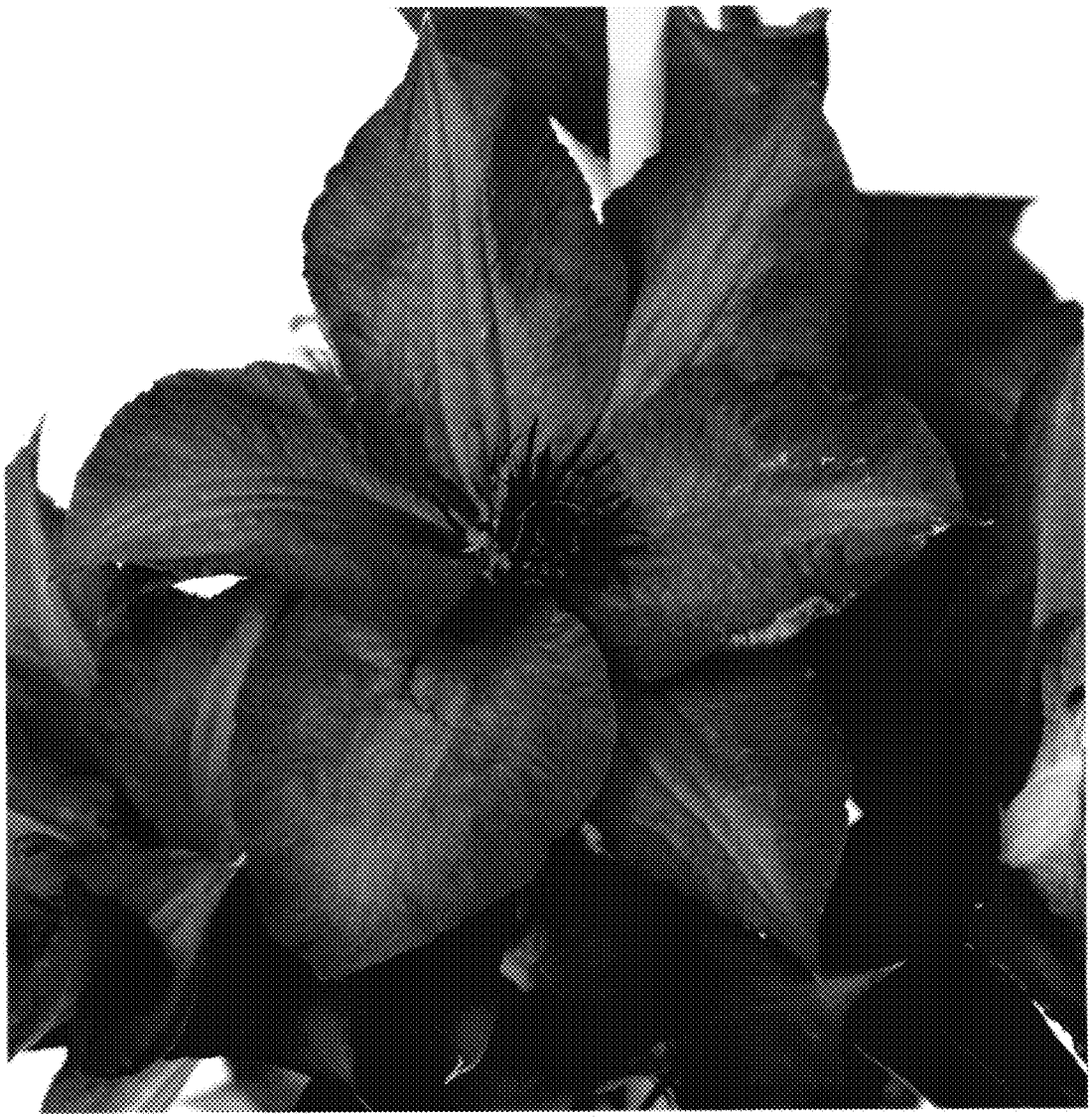
Figure 3:
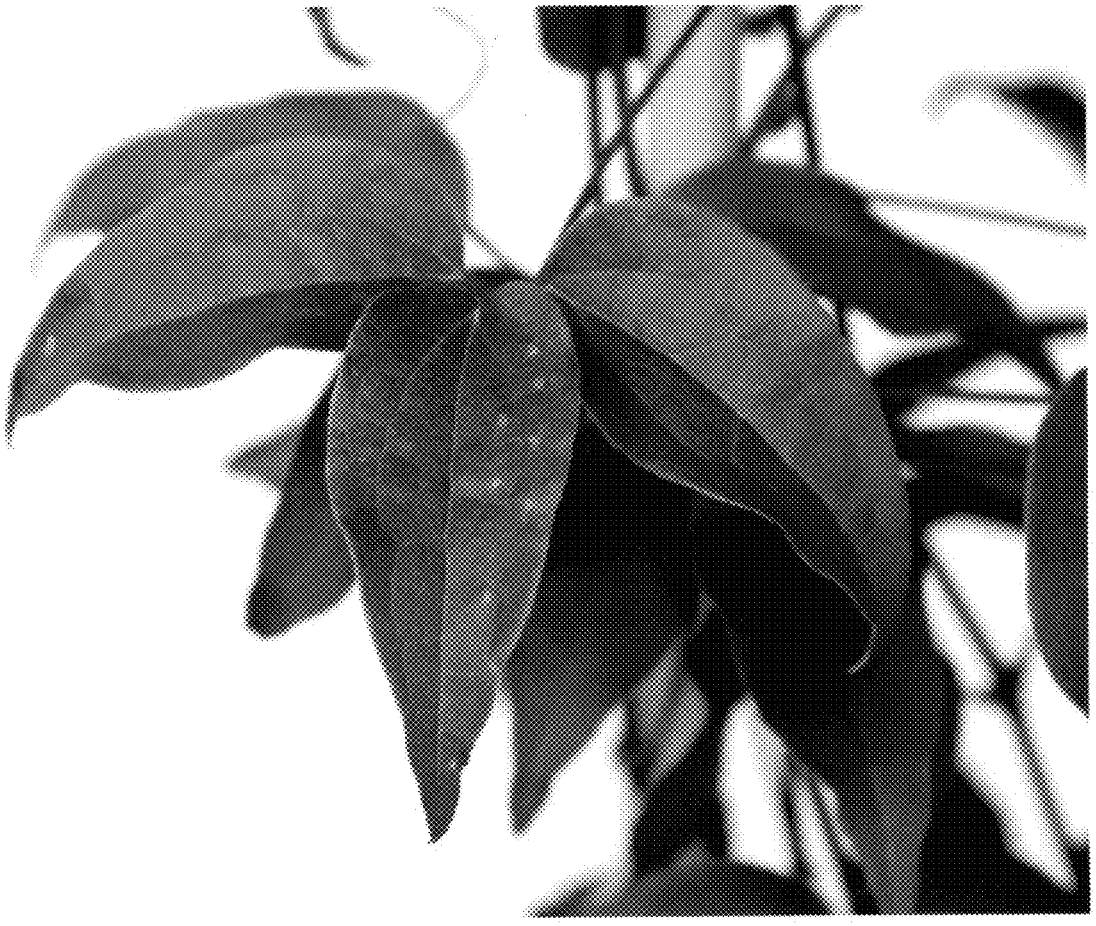

The photograph in FIG. 3 provides a close-up view of the foliage of 'Zo18197'.

The colors of the photographs are as close as possible with the digital photography techniques available, the color values cited in the detailed botanical description accurately describe the colors of the new *Clematis*.

DETAILED BOTANICAL DESCRIPTION

The following is a detailed description of 15-month-old plants as grown outdoors in 13-cm containers in Boskoop, The Netherlands. The phenotype of the new cultivar may vary with variations in environmental, climatic, and cultural conditions, as the cultivar has not been tested under all possible environmental conditions. The color determination is in accordance with The 2015 Colour Chart of The Royal Horticultural Society, London, England, except where general color terms of ordinary dictionary significance are used.

General description:

*Blooming period*.—June to September in The Netherlands.

*Plant type*.—Deciduous woody perennial.

*Plant habit*.—Low growing climber (typically tied to trellis or cane) with blooms from the base to the top of the plant.

*Height and spread*.—Height; soil level to foliar plane 67.5 cm, soil level to floral plane 70.1 cm, diameter 25.6 cm, as a 15-month old plant in a 13-cm container, up to 2 m in height when grown in the landscape.

*Hardiness*.—At least to U.S.D.A. Zones 6 to 10.

*Diseases and pests*.—No susceptibility or resistance to diseases or pests has been observed.

*Root description*.—Fleshy.

*Propagation*.—Softwood stem cuttings.

*Root development*.—An average of 6 to 8 weeks for root initiation and 5 months to produce a rooted cutting.

*Growth rate*.—Moderate.

Branch description:

*Branch shape*.—Angled.

*Branch color*.—Young; 145A, tinged darker on the sunny side 148A and 148B, mature; 164A, fading to 166B, internodes 166A, bark a blend of 166A and 200D.

*Branch size*.—Main branches; 50 cm in length, 2 mm in diameter, lateral branches; 1.9 cm in length, 1.75 mm in diameter.

*Branch surface*.—Developing and mature branches; moderately to densely covered with short pubescent hairs; 0.5 mm in length and 157D in color.

*Branch strength*.—Strong and flexible.

*Branch angle*.—Average of 80°.

*Branching*.—Average of 4 main branches, 10 lateral branches per main branch.

*Internode length*.—Main stems; average of 9.3 cm, lateral stems; 1.9 cm.

Foliage description:

*Leaf arrangement*.—Opposite.

*Leaf division*.—Compound, trifoliolate, lateral branches single.

*Leaf quantity per plant*.—Main branch; 20 (10 pairs), lateral branch; 2 (1 pair).

*Whole leaf shape*.—Broadly ovate to deltoid in outline, single leaves on lateral branches narrow ovate.

*Leaf base*.—Nearly obtuse to obtuse.

*Leaf apex*.—Narrowly acute.

*Leaf aspect*.—Slightly carinate.

*Leaf size*.—Average of 7.3 cm in length and 8.9 cm in width, single leaves on lateral branch; 5 cm in length, 2.2 cm in width.

*Leaflet quantity per compound leaf*.—Average of 3.

*Leaflet shape*.—Narrowly ovate, carinate, moderately curved downward.

*Leaflet base*.—Near obtuse to obtuse.

*Leaflet apex*.—Narrowly acute.

*Leaflet venation*.—Pinnate, upper surface; 146C, lower surface; 147C.

*Leaflet margins*.—Entire, slightly undulate, unlobed.

*Leaflet surface*.—Upper surface; smooth, glabrous, moderately glossy, lower surface; slightly to moderately glossy, moderately covered with soft pubescent hairs, 0.75 mm in length, N155A in color, margins moderately covered with soft pubescent hairs, 0.4 mm in length, N155A.

*Leaflet size*.—Average of 5.6 cm in length and 2.2 cm in width.

*Leaflet color*.—Young upper surface; 144A and 144B, young lower surface; 144A, mature upper surface NN137A, mature lower surface; a blend of 146A and 147B.

*Petioles*.—Average of 5.8 cm in length, 1 mm in diameter, strong, densely covered with short, adpressed pubescent hairs 0.5 mm in length, 156D in color, glossy surface, color; upper surface 148A, lower surface 146A.

*Petiolules*.—Average of 1.8 cm in length, 1 mm in diameter, strong, densely covered with short, adpressed pubescent hairs 0.5 mm in length, 156D in color, glossy surface, color; upper surface 148A, lower surface 146A.

Inflorescence description:

*Inflorescence type*.—Solitary.

*Inflorescence arrangement*.—Terminal on main and terminal branches.

*Peduncles*.—Average of 3.2 cm in length, vertical, 1.75 mm in diameter, color; 144A and 144B, surface is moderately glossy, strong, densely covered with short pubescent hairs 0.75 mm in length, N155A in color.

*Pedicels*.—None.

*Flower buds*.—Upright to slightly outward, lanceolate in shape, 2.4 cm in length, 8 mm in diameter, color;

177C to 177D, surface is matte and densely covered with short, pubescent hairs 0.75 mm in length, 157D in color.

*Flower fragrance*.—None.

*Lastingness of the flowers*.—14 days, self-cleaning.

*Flower quantity*.—Freely flowering, average of 38 flowers and 6 flower buds per plant.

*Flower type*.—Solitary.

*Flower aspect*.—Upright and slightly outward.

*Flower shape*.—Round and slightly star-shaped.

*Flower size*.—10.5 cm in diameter, 3 cm in depth.

*Tepal number*.—6, occasionally 4 to 5.

*Tepal shape*.—Elliptic, slightly curved downward.

*Tepal aspect*.—Rotate.

*Tepal apex*.—Apiculate.

*Tepal base*.—Cuneate.

*Tepal margin*.—Entire, finely undulate to crinkly.

*Tepal surface*.—Upper surface; very slightly glossy, moderately velvety, lower surface; matte, densely covered with very small pubescent hairs; 0.5 mm in length and NN155A in color.

*Tepal color*.—When opening upper surface; 83A to 83B, central band 86A, when opening lower surface; 90B, central band 194D, when fully open upper surface; 93B, margins N88A, central band 86B, when fully open lower surface; 90D, margins 90B, central band 76A, base 192D.

*Tepal size*.—Up to 5.8 cm in length and an average of 4.1 cm in width.

*Perianth*.—10.5 cm in length, 3 cm in diameter, rotate.

Reproductive organs:

*Gynoecium*.—Pistils; 50, 1.2 cm in length, stigma; linear in shape, 0.6 mm in length, 0.3 mm in diameter, 182B in color, style; 1.1 cm in length, color; upper portion 182A, lower portion 146D, ovary; 144B to 144C in color.

*Androecium*.—Stamens; 60, filaments; 8 mm in length, color; 193D, distal end N79A, anthers; 7 mm in length, 1 mm in width, basifixed, narrow oblong in shape, color a blend of N186A and 202A, pollen; N79A in color and low in quantity.

*Seed*.—No seed heads observed to date.

It is claimed:

1. A new and distinct cultivar of *Clematis* plant named 'Zo18197' as herein illustrated and described.

* * * * *